United States Patent [19]

Newton et al.

[11] 4,181,674

[45] Jan. 1, 1980

[54] 5-ENDO-PROTECTED HYDROXYL-BICYCLO[2,2,1]-HEPTAN-2-ONES AND PROCESS FOR PREPARING SAME

[75] Inventors: Roger F. Newton, Royston; Stanley M. Roberts, Macclesfield; David K. Rainey, Sandy, all of England; Michael J. Dimsdale, Palaiseau, France

[73] Assignee: Allen & Hanburys Limited, London, England

[21] Appl. No.: 746,740

[22] Filed: Dec. 2, 1976

[30] Foreign Application Priority Data

Dec. 3, 1975 [GB] United Kingdom ............... 49686/75

[51] Int. Cl.² ................................................ C07F 7/18
[52] U.S. Cl. ..................... 260/448.8 R; 260/345.9 P; 260/343.21; 260/345.2; 568/664; 568/670; 568/660; 560/105; 560/255; 560/106; 560/256; 560/231; 560/107; 260/590 FB; 260/586 R; 260/586 F; 260/598; 260/599; 562/503; 562/500; 562/465
[58] Field of Search ..................... 260/448.8 R, 345.9, 260/469, 483, 611 R, 611 A

[56] References Cited

U.S. PATENT DOCUMENTS

| 4,076,947 | 2/1978 | Schaub et al. ............ 260/448.8 R X |
| 4,087,620 | 5/1978 | Hayashi et al. ........... 260/448.8 R X |

*Primary Examiner*—Paul F. Shaver
*Attorney, Agent, or Firm*—Bacon & Thomas

[57] ABSTRACT

The stereospecific alkylation of a novel 3-endo-protected hydroxyl-tricyclo[3,2,0,0$^{2,7}$]heptan-6-one is described using a range of lithium-, copper or magnesium-containing organometallic reagents. This reaction provides a 5-endo-protected hydroxyl-bicyclo[2,2,1]-heptan-2-one system from which prostaglandin compounds of the F series having a protecting group at the 9-position hydroxyl group may readily be obtained by a sequence of reactions.

14 Claims, No Drawings

5-ENDO-PROTECTED HYDROXYL-BICYCLO[2,2,1]-HEPTAN-2-ONES AND PROCESS FOR PREPARING SAME

This invention relates to improvements in the synthesis of prostaglandin-type compounds. More particularly it relates to intermediates which may be of value in the stereospecific synthesis of naturally-occuring prostaglandins and their analogues.

The prostaglandins are a class of naturally occurring cyclopentane derivatives whose importance in medicine is rapidly increasing. They are biologically active in many physiological systems and they or substances which antagonise their effects have potential medicinal application in for example the control of fertility, blood pressure and inflammation, the predominant type of activity depending on the precise chemical structure. A more detailed summary of their various activities is given in British Patent No. 1,396,206.

Considerable research has been carried out not only into the synthesis of natural prostaglandins but also into attempting to prepare analogues thereof having desirable agonist or antagonist activity. In view of the complex stereochemistry of the prostaglandin molecule, such syntheses as have been developed are complicated, involving a large number of steps, and means whereby the complexity of such syntheses may be reduced have considerable value. In particular, methods are required which, while applicable to the manufacture of natural prostaglandins, are also applicable to the preparation of analogues.

We have now discovered a novel stereospecific reaction which converts an intermediate which can readily be obtained from known starting materials into a further intermediate which is particularly suitable for conversion into both natural prostaglandins and analogues thereof. The overall process using these reactions and intermediates has, inter alia, the advantage that fewer reaction stages are involved than is the case when currently known intermediates and reactions are employed.

According to one aspect of the invention, therefore, we provide a process for the preparation of a compound of formula (I)

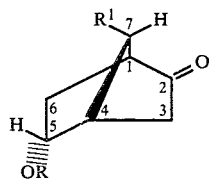

(wherein R represents an acyl, tri(hydrocarbyl)silyl, alkyl, aralkyl, cycloalkyl or tetrahydropyranyl group, and $R^1$ represents an optionally substituted $C_{1-12}$ aliphatic group), which comprises reacting a compound of formula (II)

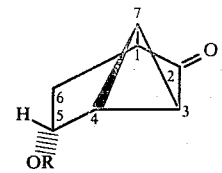

(wherein R is as defined above) with an organometallic reagent serving to introduce the group $R^1$ at the 7-position of the bicyclo[2,2,1]-heptan-2-one system.

In the formulae (I), (II), (III), (IV), (V), (VI), (VII), (VIII), set out herein, a broken line ||||||| connected to a ring substituent means that, with the ring substantially in the plane of the page, the substituent lies below the plane of the ring; a tapered line ▲ means that the substituent to which it is attached lies above the plane of the ring. Such formulae as used herein are to be understood to include both optical isomers of each of the compounds concerned as well as mixtures of said isomers, including racemates, even though the precise structure as set out relates only to one optical isomer.

Where R is an acyl group this will desirably be an alkanoyl, aralkanoyl or aroyl group, the alkanoyl group preferably containing not more than 7 carbon atoms e.g. an acetyl group and the aralkanoyl or aroyl groups preferably containing not more than 20 carbon atoms and optionally being substituted by one or more $C_{1-6}$ alkoxy groups, halogen atoms, nitro groups, $C_{1-10}$ acyloxy or $C_{2-7}$ carboalkoxy groups.

Where R is a tri(hydrocarbyl)silyl group this will carry three hydrocarbon substituents which may be the same or different selected from $C_{1-6}$ alkyl, $C_{2-6}$ alkenyl, $C_{3-7}$ cycloalkyl, $C_{7-20}$ aralkyl and $C_{6-20}$ aryl groups. Such groups will include methyl, ethyl, n-propyl, isopropyl, n-butyl, isobutyl, t-butyl, allyl, phenyl, benzyl groups. Preferred hydrocarbyl groups in the hydrocarbylsilyl group are $C_{1-5}$ alkyl e.g. methyl and t-butyl. Thus, trimethylsilyl and t-butyldimethylsilyl ethers are particularly preferred.

Where R is an alkyl group this will desirably contain up to 6 carbon atoms and may carry substituents, for example, $C_{1-6}$ alkoxy groups which may themselves be substituted, e.g. by $C_{1-6}$ alkoxy groups. Thus, for example, R may be a 2-methoxy-ethoxymethyl, methoxyethyl or 1-ethoxyethyl group.

Where R is a cycloalkyl group, this desirably contains from 3 to 7 carbon atoms.

Where R is an aralkyl group this will desirably contain up to 20 carbon atoms and will preferably be an arylmethyl group, e.g. a benzyl, diphenylmethyl or triphenylmethyl group.

Particularly useful protecting groups R include tri(hydrocarbyl)silyl groups and 2-alkoxy-ethoxymethyl groups.

The optionally substituted $C_{1-12}$ aliphatic group which $R^1$ represents may, for example, represent an optionally substituted straight or branched chain alkyl, alkenyl or alkynyl group preferably having 3 or more carbon atoms. Substituents which may be present include phenyl, substituted phenyl (e.g. substituted by methyl or trifluoromethyl), $C_{3-7}$ cycloalkyl, $C_{5-7}$ cycloalkenyl, halogen (e.g. fluorine) atoms, hydroxyl, or protected or substituted hydroxyl (e.g. aliphatic or cycloaliphatic ethers having 1-8 carbon atoms, said cycloaliphatic ethers optionally containing an oxygen atom in the ring as in the tetrahydropyranyloxy group; trihydrocarbylsilyl ethers as defined above in relation to the group R; aromatic ethers such as phenoxy or substituted phenoxy e.g. substituted by halogen, methyl or trifluoromethyl; or acyloxy derivatives of $C_{1-4}$ aliphatic acids). The alkyl, alkenyl or alkynyl chain may, if desired, be interrupted by a keto- or protected keto- (e.g. ketal or cyclic ketal) group, or part of the chain may form part of a cycloalkyl or cycloalkenyl ring system.

The group $R^1$ is preferably a group of formula:

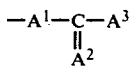

where
$A^1$ is trans $-CH=CB^1-$ (where $B^1$ is a hydrogen atom or methyl group); $-CH_2-CH_2-$; or $-C\equiv C-$;
$A^2$ is oxygen;

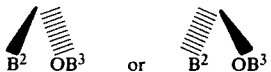

(where $B^2$ is a hydrogen atom or a methyl or ethyl, vinyl or ethynyl group and $B^3$ is hydrogen or a hydroxy protecting group such as the group R as defined above); and $A^3$ is a branched or unbranched $C_{1-9}$ alkyl radical optionally substituted with an oxo group, a hydroxy or protected hydroxy group or halogen atoms (e.g. fluorine);
a branched or unbranched $C_{2-9}$ alkenyl radical;
or a group $-B^4.B^5$ or $-B^4.O.B^5$
(where $B^4$ is $C_{1-5}$ alkylene, $B^5$ is $C_{5-7}$ cycloalkyl or phenyl optionally substituted by halogen atoms (e.g. fluorine), $C_{1-4}$ alkyl or $C_{1-4}$ haloalkyl (e.g. trifluoromethyl)).

Particularly preferred compounds of formula I include those in which $R^1$ represents a group of formula

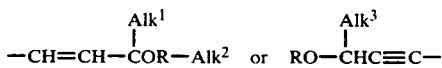

wherein R has the meaning given in claim 1 or is hydrogen, Alk$^1$ represents hydrogen or an alkyl group having up to 2 carbon atoms, Alk$^2$ represents an alkyl group having up to 9 carbon atoms and Alk$^3$ represents hydrogen or an alkyl group having up to 9 carbon atoms.

The organometallic reagent will most desirably be a copper-containing reagent of the type Li[$R^2$ Cu $R^{1a}$], wherein $R^{1a}$ is as defined above for $R^1$ other than an ethynyl or 2-substituted ethynyl group and $R^2$ is the same as $R^{1a}$ or is an ethynyl or 2-substituted ethynyl group; or a lithium aluminium complex of the type Li Al $(R^3)_3R^{1b}$ where the groups $R^3$ represent alkyl groups which may be the same or different and $R^{1b}$ represents an alk-1-enyl group; or a Grignard reagent $R^{1c}$Mg X, preferably a copper catalysed Grignard reagent, wherein $R^{1c}$ is as defined above for $R^1$ including an ethynyl or 2-substituted ethynyl group and X is a halogen atom e.g. chlorine, bromine or iodine; or an organo copper reagent Cu($R^{1a}$)$_2$, where $R^{1a}$ is as defined above, in the presence of a metal salt Mg $X_2$ or LiX where X has the meaning given above; or a lithium acetylide of the type LiR$^{1d}$ where R$^d$ is an ethynyl or 2-substituted ethynyl group.

The group $R^2$ as indicated above preferably represents an ethynyl or 2-substituted ethynyl group e.g. a 2-alkyl-ethynyl group having 3-6 carbon atoms, for example a pent-1-ynyl group. This preference is a consequence of the nature of the reaction wherein only one of the carbon-containing side-chains in the copper-containing organometallic reagent is transferred to the tricyclo compound (II). The remaining side chain is effectively wasted. It is therefore desirable, particularly when $R^1$ is an expensive and lengthy side-chain, not to waste side-chain material and to employ as $R^2$ a group which bonds more strongly to the metal than $R^1$. Ethynyl and 2-substituted ethynyl groups are particularly suitable in this regard and for the same reason it is essential that the side-chain $R^1$ does not contain these groups in the terminal position when a copper-containing reagent is used.

The copper-containing reagent Li[$R^2$CuR$^{1a}$] will itself generally be prepared in solution prior to the reaction by methods well known in the art. For example, where $R^2$ is an ethynyl or 2-substituted ethynyl group, the reagent may be prepared by admixture of the copper acetylide Cu $R^2$ with a lithium alkyl such as n-butyl lithium and the compound $R^{1a}$X where X is a halogen atom, in a hydrocarbon and/or ether solvent.

The copper-containing reagent Li[$R^2$CuR$^{1a}$] will also desirably contain additional solubilising groups thus having the formula Li[$R^2$CuR$^{1a}$($R^4$)$_2$], where $R^4$ is a solubilising group. Such solubilising groups may take a variety of forms but phosphorus-containing organic groups are preferred. Particularly preferred groups are tris(dialkylamino)phosphine, trialkyl phosphine and trialkyl phosphite groups such as tris-dimethylaminophosphine, tri-n-butyl-phosphine and trimethyl phosphite. Copper-containing reagents having such solubilising groups will desirably be prepared in situ by methods known in the art e.g. by admixture of (i) a solution containing a hexalkyl phosphorus triamide and a copper acetylide CuR$^2$ with (ii) a lithium alkyl and a compound of formula R$^{1a}$X.

Copper-catalysed Grignard reagents are a further useful source of carbon-containing side chains. Use of reagents of this type has the further advantage that C-terminal alkynyl groups may be added to the tricyclo compound (II). The catalyst may be added in the form of either a cuprous or cupric salt e.g. a cuprous halide such as a cuprous iodide, bromide or chloride or copper acetate.

The tricyclo compound of formula (II), which is preferably separated from impurities associated with its preparation prior to reaction, is generally reacted with the organometallic reagent at below ambient temperature. Reaction of the tricyclo compounds with the copper-catalysed Grignard reagents will desirably be effected at or around 0° C., whereas reaction with the copper-containing reagents will desirably be effected at much lower temperatures e.g. at from −10° C. to −85° C., preferably below −55° C. e.g. around −78° C.

Solvents which may be used for the reaction will be those conventionally used in organometallic chemistry and will be aprotic and preferably polar. Suitable solvents include ethers, e.g. diethyl ether, tetrahydrofuran, dioxan, dimethoxyethane or hydrocarbons, e.g. hexane or petroleum ether.

According to a further aspect of the invention we provide compounds of the general formula (I) wherein R and $R^1$ have the meanings given above.

According to a still further feature of the invention we provide compounds of the general formula (II) wherein R has the meaning given above. These compounds are of particular value in that they are capable of reactions other than the one detailed above, whereby still further prostaglandin analogues can be prepared.

Compounds of general formula (II) may be prepared by reacting a compound of the general formula (III)

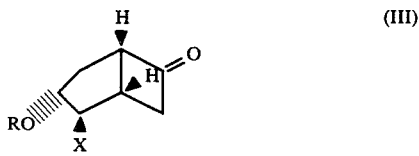

wherein R is as defined above and X represents a halogen (e.g. chlorine, bromine or iodine) atom with a weakly nucleophilic strong base in a substantially aprotic solvent and isolating the desired product of formula (II). Examples of bases include alkoxides of alkali metals such as sodium or potassium e.g. the methoxide and especially tertiary alkoxides e.g. the t-butoxide; such alkoxides are preferably reacted in a hydrocarbon solvent e.g. benzene or toluene. A minor amount of a lower tertiary alkanol, e.g. t-butanol, may be added to improve solubility. The amides and silazides of an alkali metal, e.g. sodium hexamethyldisilazide, may also be used; suitable solvents for these bases are ethers such as diethyl ether. Other bases which may be used include very basic amines, for example 1,4-diazabicyclo(3,3,-0)oct-1-ene; convenient solvents include ethers e.g. alkyl or cycloalkyl ethers, for example diethyl ether, dioxan or tetrahydrofuran.

Reaction may be effected at a temperature in the range $-80°$ to $+30°$ C., preferably $-70°$ to $0°$ C.

The compounds of formula (III) in which OR is an ether or acyloxy group and corresponding OH derivatives may be prepared by for example, the reaction of a compound of formula (IV).

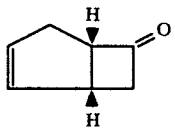

with a molecular halogen such as chlorine or an N-haloamide or N-haloimide, for example an N-haloacetamide or an N-halo succinimide e.g. N-bromoacetamide or N-bromosuccinimide, in the presence of an alcohol (to give a compound in which OR is an ether group derived from the alcohol), a carboxylic acid (to give a compound in which OR is acyloxy) or water (to give the -OH compound). The latter can be acylated or etherified, e.g. silylated or tetrahydropyranylated, to give other compounds of formula (III). In the case of water, it is preferable to carry out the reaction in an aprotic solvent, such as acetone or tetrahydrofuran.

Reaction may be effected at ambient temperature. It is possible to exchange the group R by its elimination, preferably under acid conditions, and subsequent acylation or etherification to produce a compound of formula (III) in which R is a different acyloxy group or ether group.

The compounds of formula (I) may be further reacted, according to another aspect of the invention to produce further prostaglandin precursors of formula (V)

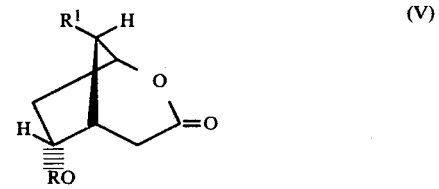

wherein R and $R^1$ are as defined above, using a Baeyer-Villiger-type oxidation. This will conveniently be effected using a peracid e.g. peracetic acid, trifluoroperacetic acid, performic acid, perbenzoic acid, a halogenated perbenzoic e.g. m-chloroperbenzoic acid, or a persulphuric acid. A preferred reagent is peracetic acid. Where the group RO is stable to the acid and alkaline conditions employed it is also possible to use hydrogen peroxide in acetic acid or alkaline hydrogen peroxide. In the latter case the initial product is a hydroxy acid salt which, on acidification, forms the desired lactone of formula (V).

The reaction may be carried out at a temperature in the range $-50°$ to $+100°$ C., preferably $-0°$ to $+30°$ C.

Preferably the oxidations using peracetic, pertrifluoroacetic or performic acid are carried out in the corresponding carboxylic acid as solvent, and in the presence of an alkali metal salt of the carboxylic acid.

The oxidations using perbenzoic or halogenated perbenzoic acids will desirably be effected in an inert solvent e.g. a halogenated hydrocarbon, such as methylene dichloride or chloroform at a temperature between ambient temperature and about $0°$ C. The presence of a mild organic base to neutralise any carboxylic acid formed is also desirable e.g an alkali metal carbonate or bicarbonate.

It is clearly desirable that any groupings in the substituent $R^1$ which might be effected by the peroxo reagent, e.g. keto groups, are protected in a suitable manner, e.g. by ketal formation.

Compounds of general formula (V) in which R is other than an acyl group when $R^1$ is a $C_{4-12}$ alken-1-yl group wherein the alken-1-yl group carries an keto or protected keto group adjacent the double bond, are new compounds and constitute another feature of the invention.

Partial reduction of a lactone (V) to give a lactol (VI)

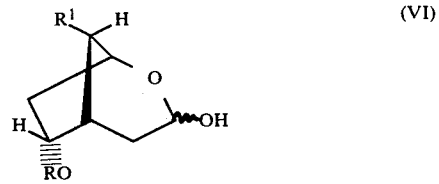

which, it will be seen, is a cyclic hemiacetal of the aldehyde (VII)

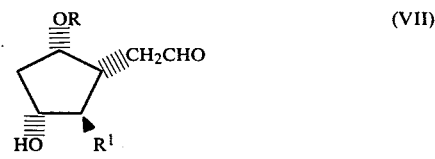

and exists in equilibrium with the aldehyde form, may be effected using a metal hydride reducing agent such as a complex metal hydride reducing agent e.g. a dialkylaluminium hydride, for example diisobutyl aluminium hydride, or an alkylborane e.g. di-isoamyl borane, in a suitable inert solvent, e.g. a hydrocarbon solvent such as hexane.

The lactol (VI) and aldehyde (VII) are of considerable value in the preparation of natural prostaglandins, in particular those of the F series. It is of particular value that the protected compound of formula (VI) or (VII) allows the synthesis of prostaglandins of the F series which have a protecting group on the hydroxyl group at the 9-position and a hydroxyl group at the 11-position, which compounds have not previously been prepared and are not readily accessible from the natural prostaglandin.

Natural prostaglandin derivatives or analogues thereo may be prepared from the equilibrium mixture of compounds (VI) and (VII) by reaction of this mixture with an appropriate Wittig reagent.

Thus, for example, compounds of the formula (VIII)

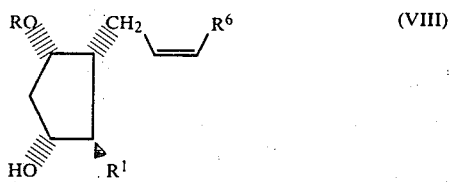

(VIII)

(wherein R and $R^1$ have the above meanings and $R^6$ represents a straight or branched saturated or unsaturated $C_{1-10}$ alkyl group, which group may be substituted by a carboxyl, esterified carboxyl, cyano, hydroxyl, or protected hydroxyl group) may be prepared by reaction of the equilibrium mixture of compounds (VI) and (VII) with a phosphorane compound of the formula $(R^5)_3P=CHR^6$ (wherein $R^6$ has the above meaning and $R^5$ is an alkyl, preferably lower alkyl group containing 1-4 carbon atoms or is an aryl group, preferably a monocyclic aryl group such as a phenyl group) conveniently in a solvent, for example a hydrocarbon, (desirably benzene, or toluene), an ether (desirably tetrahydrofuran), a dialkylsulphoxide (desirably dimethylsulphoxide), an alcohol or a halogenated hydrocarbon.

The phosphorane may conveniently be prepared by reacting the phosphonium salt $(R^5)_3P^+CH_2R^6X^-$, where X is a halogen atom, with a suitable base for example sodium hydride, an organo lithium e.g. butyl lithium or an alkali metal alkoxide, for example a sodium or potassium t-alkoxide, e.g. sodium t-butoxide or t-amyloxide.

The compounds of formula (VIII) prepared in this manner carry an ether or acyl protecting group R (and may further carry protecting groups in side-chains) and may be deprotected by conventional techniques to yield natural prostaglandins or analogues thereof. This reaction will desirably be carried out as the last stage in the synthetic route though it will be understood that it may be convenient to deprotect at an earlier stage of the synthesis in order to introduce a different group R.

The compounds of formula (III) wherein R and X are as defined above, R however being restricted to tri(hydrocarbyl)silyl when X is bromine, and also the compounds of formulae (VI), (VII) and (VIII) as defined above, are all new compounds which constitute further features of the invention.

The invention will now be more particularly described in the following Preparations and Examples which should not be construed as limiting the invention. Throughout the Preparations and Examples, all temperatures are in °C.

Preparation 1

3-Endo-hydroxy-2-exo-bromobicyclo[3,2,0]heptan-6-one

To bicyclo[3,2,0]hept-2-en-6-one, (1.5 g) in 25 ml of acetone and 6 ml of water was slowly added N-bromoacetamide (3 g) with stirring. The homogeneous solution was left to stand for 12 h, after which time a further 10 ml of water were added and the acetone removed on a rotary evaporator. The residue was taken up in chloroform, the organic layer was washed with water (6×20 ml) and the combined aqueous fractions were extracted with chloroform (3×30 ml). After drying and evaporation of the chloroform extracts, 3-endo-hydroxy-2-exo-bromobicyclo[3,2,0]heptan-6-one was obtained as a white solid. Recrystallisation from petrol ether and a trace of benzene gave white crystals of title compound (2.55 g) m.p. 87°–89° C.; $\nu_{max}$ 3400, 1770 cm$^{-1}$; $\tau$ (CDCl$_3$), 5.32 (1H), 5.64 (1H), 6.2 (1H), 6.78 (2H), 7.28 (1H, dd J 16.0, 8.0 Hz, 4-exo-H) and 7.62 (1H, dd J 16.0 Hz).

Preparation 2

3-Endo-methoxy-2-exo-bromobicyclo[3,2,0]heptan-6-one

To bicyclo[3,2,0]hept-2-en-6-one (5 g) in methanol (70 ml) was added N-bromoacetamide (6.6 g) with stirring. The homogeneous solution was left to stand for 12 h, and then taken up in chloroform. After repeated washing with water and back extraction of the aqueous fractions with chloroform, drying and evaporation gave 3-endo-methoxy-2-exo-bromobicyclo[3,2,0]heptan-6-one as a yellow oil in quantitative yield. This was pure enough for further reaction although vacuum distillation gave pure title compound as a clear oil (9.0 g) b.p. 90° C., 0.02 mm; $\nu_{max}$ 2950, 1780 cm$^{-1}$.

Preparation 3

3-Endo-acetoxy-2-exo-bromobicyclo[3,2,0]heptan-6-one

N-Bromoacetamide (8.0 g) was added with stirring to bicyclo[3,2,0]hept-2-en-6-one (6.0 g) in glacial acetic acid (50 ml). the homogeneous solution was left to stand for 12 h and then the volume of acetic acid was reduced to about 15 ml on a rotary evaporator. The residue was taken up in chloroform and washed with water (3×20 ml). The separate organic and aqueous fractions were neutralized with saturated sodium bicarbonate solution. The combined aqueous layers were then washed twice with chloroform. After drying and evaporation of the organic layers 3-endo-acetoxy-2-exo-bromobicyclo[3,2,0]heptan-6-one was obtained as a yellow oil pure enough for further reaction.

Vacuum distillation gave title compound as a clear oil, turning to a waxy solid on standing (13.0 g) b.p. 83° C., 0.04 mm Hg; $\nu_{max}$ 2970, 1770 cm$^{-1}$.

Preparation 4

Tetrahydropyranyl ether of 3-endo-hydroxy-2-exo-bromobicyclo[3,2,0]heptan-6-one Dihydropyran (1.5 g) was added to a solution of 3-endo-hydroxy-2-exo-bromobicyclo[3,2,0]heptan-6-one (2.0 g) in benzene (12 ml). The reaction was catalysed by the addition of two drops of phosphoryl chloride (phosphorus oxychloride). After stirring at room temperature for 3 h the solution was treated with triethylamine (four drops) and was then washed with a saturated solution of brine. After back extraction of the aqueous layers with benzene the combined organic layers were dried and evaporated to give a viscous yellow oil. Vacuum distillation gave pure title compound (2.3 g) b.p. 110° C., 0.05 mm; $\nu_{max}$ 2960, 1785 cm$^{-1}$.

Preparation 5

2-exo-Bromo-3-endo-(t-butyldimethylsilyloxy)-bicyclo[3,2,0]heptan-6-one 2-exo-Bromo-3-endo-hydroxybicyclo[3,2,0]heptan-6-one (12.30 g), t-butyldimethylchlorosilane (11.30 g) and imidazole (10.2 g) were stirred together in dry DMF (70 ml) for 17 hours.

The solution was diluted with water (100 ml) and was extracted with b.p. >40° light petroleum (3×50 ml). The extracts were combined, washed with water (2×50 ml) and were dried (MgSO$_4$). Evaporation of the solvent gave 19.62 g of a light brown oil which was distilled in vacuo. After a forerun, b.p. ~35°/1–0.5 mm, title compound distilled as a colourless oil, (14.4 g) b.p. 91°–105°/0.1–0.17 mm, which crystallized on standing, m.p. 48°–52°.

Preparation 6

2-exo-Bromo-3-endo-(triphenylsilyloxy)-bicyclo[3,2,0]heptan-6-one

A solution of 2-exo-bromo-3-endo-hydroxybicyclo[3,2,0]heptan-6-one (6.9 g), triphenylsilyl chloride (12.0 g), imidazole (6.0 g) and dry dimethylformamide (200 ml) was stirred at room temperature for 20 hours. The mixture was poured into water (200 ml) and extracted successively with ether (50 ml) and ethyl acetate (200 ml). The combined organic extracts were washed with water (100 ml), saturated sodium chloride and dried (MgSO$_4$). Removal of solvent gave a white solid which was recrystallised from isopropanol to give title compound as a white crystalline solid (12.9 g) m.p. 114°–116°.

Preparation 7

2-exo-Bromo-3-endo-(benzyloxy)-bicyclo[3,2,0]heptan-6-one

A solution of bicyclo[3,2,0]hept-2-en-6-one (36.8 g) in benzyl alcohol (240 ml) cooled in an ice/water bath was treated with N-bromosuccinimide (60.5 g) portionwise over 1 hour. The resulting solution was stirred in the dark at room temperature for 16 hours, diluted with ether (700 ml), washed with water (4×250 ml) and dried (MgSO$_4$). Removal of ether gave a pale yellow liquid (292 g) which was dissolved in dichloromethane (266 ml) and light petroleum (b.p. 60°–80°) (1.77 liters) and stirred with pulverised anhydrous calcium chloride (585 g) for 20 hours at room temperature. Filtration and removal of solvent gave an oily solid (89.4 g). Crystallisation from ether (100 ml) at −15° overnight gave title compound (48.2 g) as a colourless crystalline solid, m.p. 57°–58.5°.

Preparation 8

2-exo-Bromo-3-endo-(tri-n-butylsilyloxy)-bicyclo[3,2,0]heptan-6-one

A solution of 2-exo-bromo-b 3-endo-hydroxybicyclo[3,2,0]heptan-6-one (1.0 g), tri-n-butylsilyl chloride (1.25 g), imidazole (0.85 g) in dry dimethylformamide was allowed to stand at room temperature for 20 hours. The mixture was poured into water (30 ml), extracted with ether (15 ml) and light petroleum spirit (b.p. 60°–80°) (2×20 ml). The combined organic extracts were chromatographed on silica (50 g) with ethyl acetate/light petroleum (1:4) as eluant to yield the crude product as a colourless oil (1.95 g). A portion (0.75 g) was distilled at 210–211/0.09 mm to yield the pure title compound (0.69 g) as a colourless oil.

Analysis Found: C56.76; H, 8.80; C$_{19}$H$_{35}$BrSiO$_2$. requires C56.60; H, 8.69%.

Preparation 9

1-Iodo-3-methyl-oct-1-en-3-ol

Methyl iodide (25.4 g) in dry ether (20 ml) was added slowly to magnesium metal (4.35 g) in dry ether (40 ml) under dry nitrogen. After the initial vigorous reaction, the addition rate was controlled to maintain a steady reflux. The mixture was then refluxed for a further ½ hr. The solution was transferred under nitrogen to a dropping funnel, and added slowly to a solution of the 1-iodo-oct-1-en-3-one (30.0 g) in dry ether (150 ml) at 0°. After addition of 85% of the Grignard reagent t.l.c. (silica gel-ethyl acetate/petroleum ether (1:9)-molybdophosphoric acid) showed that no starting material remained.

The mixture was quenched in saturated ammonium chloride solution (750 ml), separated and the aqueous layer washed with ether (3×200 ml). The combined organic layers were washed with sat. sodium thiosulphate solution (200 ml), water (200 ml), dried (anhydrous MgSO$_4$) and evaporated to give the title compound as a dark brown oil (19.4 g) which was used directly in Preparation 10.

TLC R$_f$ 0.35 (silica gel- ethyl acetate/light petroleum ether (1:9)-molybdophosphoric acid)

Preparation 10

1-Iodo-3-methyl-3-(trimethylsilyloxy)-oct-1-ene

The crude alcohol (Preparation 9) (14.8 g), imidazole (9.38 g) and trimethylsilyl chloride (8.75 ml) were shaken in dry dimethylformamide (20 ml) and allowed to stand for 0.5 hr. when t.l.c. (silica-light petroleum (60°–80°)/ethyl acetate (9:1)-molybdophosphoric acid) showed that no starting material remained. The mixture was poured into water (100 ml) and extracted with light petroleum (40°–60°) (3×100 ml). The combined extracts were washed with water (2×100 ml), dried (MgSO$_4$) and evaporated to give the title compound as a yellow oil (17.7 g).

Column chromatography on silica gel (Merck 7734, 350 g) with light petroleum (60°–80°) as eluent taking 75 ml fractions, followed by evaporation of solvent, gave the title compound as a colourless oil (fractions 6–40) (7.7 g).

TLC R$_f$ 0.88 (silica gel-petroleum ether (b.p. 60°-80°)molybdophosphoric acid).

Preparation 11

3-endo-Hydroxy-2-exo-chloro-bicyclo[3,2,0]heptan-6-one

Bicyclo[3,2,0]hept-2-en-6-one (1.0 g) was added dropwise to chlorine water (10 ml) and the resultant mixture was shaken for one hour and allowed to stand overnight at room temperature. The solution was extracted with chloroform (50 ml) and the extracts were washed once with saturated sodium bicarbonate solution (20 ml). After drying and evaporation of the solvent the crude chlorohydrin was obtained as a slightly yellow oil. Chromatography on silica (50 g) with ethyl acetate/light petroleum (1:4) as eluant yeilded the title compound as a colourless oil (0.4 g)

Preparation 12

3-endo-Acetoxy-2-exo-chloro-bicyclo[3,2,0]heptan-6-one

Acetic anhydride (1.0 g) was added dropwise and with stirring to a solution of 3-endo-hydroxy-2-exo-chloro-bicyclo [3,2,0]heptan-6-one (0.4 g) in pyridine (6 ml). The mixture was stirred at room temperature for 48 hours and extracted with chloroform (50 ml). The extracts were washed once with 4 N sulphuric acid (20 ml) and then with saturated sodium bicarbonate solution (20 ml). After drying and evaporation the crude product was distilled (b.p. 97°-101° C. at 0.1 mm), to afford title compound (0.4 g) as a colourless oil. M+ (calculated) 202.0393—(found) 202.0395.

Preparation 13

3-endo-Acetoxy-2-exo-iodo-bicyclo[3,2,0]heptan-6-one

Bicyclo[3,2,0]hept-2-en-6-one (1.0 g) in glacial acetic acid (20ml) was treated with iodine (1.35 g) and KIO$_3$ (570 mg). After stirring for 24 hours at room temperature the mixture was extracted with ether (50 ml). The extracts were washed successively with saturated sodium chloride solution (50 ml), saturated sodium bicarbonate solution (50 ml), 1 N sodium thiosulphate solution (50 ml) and saturated sodium chloride solution (50 ml). After drying and evaporation the crude product was chromatographed on silica (SiO$_2$) (60 g). Elution with ethyl acetate/light petroleum (1:4) gave the pure title compound (1.8 g) as a slightly yellow oil. M+(calculated) 293.9755 (found) 293.9755

EXAMPLE 1

3-endo-Acetoxytricyclo[3,2,0,0$^{2,7}$]heptan-6-one

Potassium t-butoxide (9 g) was stirred under nitrogen in dry benzene (360 ml) while cooled by an ice bath for ½hour. Dry t-butanol (30 ml) was then added followed by dropwise additiion of 2-exo-bromo-3-endo-acetoxybicyclo[3,2,0]heptan-6-one (9.9 g) in dry benzene (30 ml) at such a rate as to keep the temperature below 10°. The solution was stirred (1½ hours) at 10°-15° and was then poured into dichloromethane (ca. 500 ml). The solution was filtered from the precipitated solid and the filtrate was evaporated to dryness in vacuo at room temperature to give the crude product as a brown oil (4.68 g) which crystallised on standing. This was recrystallised from cold ether/light petroleum b.p. <40° to give needles of title compound (4.0 g).

The following compounds were similarly prepared:

3-endo-Methoxytricyclo[3,2,0,0$^{2,7}$]heptan-6-one—light brown oil.
3-endo-t-Butyldimethylsilyloxytricyclo[3,2,0,0$^{2,7}$]heptan-6-one—light brown oil.

The title compound was also prepared in a similar fashion from 2-exo-chloro-3-endo-acetoxybicyclo[3,2,0-]heptan-6-one (2 g) and from 2-exo-iodo-3-endo-acetoxybicyclo[3,2,0]heptan-6-one (2.9 g). Yields: 0.9 g and 1.2 g respectively.

EXAMPLE 2

7-anti(3-t-Butyldimethylsilyloxy-1-octenyl)-5-endo-t-butyldimethylsilyloxybicyclo[2,2,1]heptan-2-one 3-t-Butyldimethysilyloxy-1-iodo-1-octene (6.07 g) in dry light petroleum (b.p. 60°-80°, 50 ml) was cooled, under nitrogen, to −70°, 2.1 M n-butyllithium in hexane solution (8.0 ml) was added and the solution was stirred ½ hour at −70°. A solution of cuprous n-propyl acetylide (2.15 g) in ether (25 ml) and hexamethylphosphorus triamide (6.04 ml) was added to this solution which was stirred for a further 15 minutes at −70°. 3-endo-t-Butyl-dimethylsilyloxytricyclo[3,2,0,0$^{2,7}$]heptan-6-one (3.7 g) in dry ether (ca. 50 ml) was then added to the orange solution which was stored at −70° for 1½ hours, and warmed to −30°. The cold reaction mixture was poured into saturated ammonium chloride solution (40 ml) and shaken. The organic layer was removed and the aqueous layer was extracted once with ether (20 ml). The combined organic solutions were then shaken with ice-cold 2% sulphuric acid (ca. 200 ml) and the mixture filtered through hyflo to remove precipitated copper salts. The organic layer was removed, washed once with 8% sodium bicarbonate solution and dried (MgSO$_4$). Evaporation of the solvent gave an oil which was chromatographed on silica in light petroleum containing increasing amounts of ethyl acetate. Light petroleum eluted unreacted octene side chain and impure product was eluted with ethyl acetate/light petroleum (5:95) as a pale yellow oil (5.26 g). Short path distillation afforded pure title compound as a pale yellow oil (3.29 g) b.p. ca. 180°-200°/0.15 mm.

Similarly prepared were:
7-anti-(3-t-Butyldimethylsilyloxy-1-octenyl)-5-endo methoxybicyclo [2,2,1]heptan-2-one, b.p. ca. 160°/0.15 mm.
7-anti-(3-t-Butyldimethylsilyloxy-1-octenyl)-5-endo-acetoxybicyclo [2,2,1]heptan-2-one, b.p. ca. 190°/0.15 mm

EXAMPLE 3

7-anti-Butyl-5-endo-methoxybicyclo[2,2,1]heptan-2-one

A solution of cuprous n-propyl acetylide (3.88 g) in ether (30 ml) and hexamethylphosphorus triamide (11.0 ml) was added, under nitrogen, to a solution of 2.1 M n-butyllithium in hexane solution (14.1 ml) in ether (20 ml) at −70° and stirred at −70° for 15 min. 3-endo-Methoxytricyclo[3,2,0,0$^{2,7}$]heptan-6-one (4.1 g) in ether (30 ml) was then added to the orange solution which was stored at −70° for 40 min. Water (ca. 100 ml) was added to the cold solution and shaken. The organic layer was removed and shaken with ice cold 2 N hydrochloric acid (100 ml) and the mixture filtered through hyflo to remove precipitated copper salts. The organic layer was removed, washed with 2 N hydrochloric acid, water and dried (Na$_2$SO$_4$). Evaporation of the solvent gave an oil which was chromatographed on silica in light petroleum (b.p. 60°-80°) containing increasing amounts of ethyl acetate. Impure title compound was eluted with ethyl acetate/light petroleum (1:9) as a pale yellow oil (2.3 g). Short path distillation afforded pure title compound as a colourless oil b.p. ca. 80°–85°/0.05 mm;

Rf 0.47 (silica-ethyl acetate/petroleum ether (b.p. 60°–80°) (1:9)-dinitrophenyl hydrazine spray) $\nu_{max}$ (CHBr$_3$) 1740 cm$^{-1}$.

EXAMPLE 4

8-anti-Butyl-6-endo-methoxy-2-oxabicyclo[3,2,1]octan-3-one (i) A 28% hydrogen peroxide solution (6.0 ml) was added dropwise to a stirred solution of 7-anti-butyl-5-endo-methoxybicyclo[2,2,1]heptan-2-one (0.5 g) in glacial acetic acid (25 ml) containing sodium acetate (1.25 g) and stirred at ambient temperature for 24 hr. Solid sodium sulphite was added to the solution until a negative reaction with starch iodide paper was obtained. The solution was diluted with water (50 ml) and extracted with ether (3×30 ml). The combined extracts were washed with 8% sodium bicarbonate solution and water. After drying (Na$_2$SO$_4$) the solvent was evaporated to afford a pale yellow oil (0.41 g) which was purified by chromatography on silica with ether acetate/light petroleum (2:3) as eluent to yield title compound as a pale yellow oil (0.2 g); Rf 0.59 (silica-ethyl acetate/light petroleum (b.p. 60°–80°) (2:3)-iodine vapour); $\nu_{max}$ (film) 1738 cm$^{-1}$ GLC analysis showed product to contain 94.4% of required isomer.

(ii) m-Chloroperbenzoic acid (0.3 g of 85% material) was added portionwise to a stirred mixture of 7-antibutyl-5-endo-methoxybicyclo[2,2,1]heptan-2-one (0.196 g) and potassium hydrogen carbonate (0.3 g) in dichloromethane (10 ml) and stirred at ambient temperature for 22 hr. The solution was washed with 10% sodium sulphite solution, 8% sodium bicarbonate solution and water. After drying (Na$_2$SO$_4$) the solvent was evaporated to give the crude product as a colourless oil (0.18 g). This product was purified by chromatography on silica using ethyl acetate/light petroleum (2:3) as eluent to afford title compound as a pale yellow oil (0.08 g).

GLC analysis showed product to contain 80.5 % of required isomer.

(iii) A mixture of potassium persulphate (0.81 g), concentrated sulphuric acid (0.57 ml) and ice (3.7 g) was added to a stirred solution of 7-anti-butyl-5-endo-methoxybicyclo[2,2,1]heptan-2-one (0.196 g) in glacial acetic acid (20 ml). Stirring was continued at ambient temperature for 22 hrs. Solid sodium bicarbonate was then added until effervescence ceased and the solution was diluted with water (50 ml). The solution was extracted with ether (3×25 ml) and the combined extracts washed with 8% sodium bicarbonate solution (3×25 ml), 10% sodium sulphite solution (25 ml) and water (25 ml). After drying (Na$_2$SO$_4$) the solvent was evaporated to give a colourless oil (0.103 g) which was chromatographed on silica with ethyl acetate/light petroleum (2:3) as eluent to afford pure title compound (0.025 g).

GLC analysis showed product to contain only the required isomer.

EXAMPLE 5

8-anti(3-t-Butyldimethylsilyloxy-1-octenyl)-6-endo-t-butyldimethylsilyloxy-2-oxabicyclo[3,2,1]octan-3-one (i) A 28% solution of hydrogen peroxide (3 ml) was added to a solution of 7-anti(3-t-butyldimethylsilyloxy-1-octenyl)-5-endo-t-butyldimethylsilyloxybicyclo[2,2,1]heptan-2-one (0.48 g) in acetic acid (25 ml) with sodium acetate (0.5 g) and allowed to stand at ambient temperature for 21½ hr. The solution was diluted with water and solid sodium sulphite added. This mixture was extracted with light petroleum ether b.p. <40° (3×10 ml). The combined extracts were washed twice with 9% sodium bicarbonate solution, twice with saturated sodium sulphite solution (acidified) and with water. After drying (MgSO$_4$) evaporation of the solvent gave a colourless oil (0.44 g) which was purified by chromatography on silica with ethyl acetate/petroleum ether (1:9) as eluent to yield title compound as a colourless oil (0.24 g). Rf 0.31 (silica-ethyl acetate/light petroleum (b.p. 60°–80°) (1:9)-molybdatophosphoric acid); $\nu_{max}$ (film) 1738 cm$^{-1}$.

Structure confirmed by H$^1$ and C$^{13}$ NMR spectroscopy.

(ii) A mixture of m-chloroperbenzoic acid (0.254 g of 85% material), potassium hydrogen carbonate (0.15 g) and 7-anti(3-t-butyldimethylsilyloxy-1-octenyl)-5-endo-t-butyldimethylsilyloxybicyclo[2,2,1]heptan-2-one (0.48 g) in dichloromethane (20 ml) was stirred at ambient temperature for 40 hr. A further quantity of m-chloroperbenzoic acid (0.05 g) was added and stirring continued for a further 24 hr. The reaction mixture was filtered and the filtrate washed with saturated sodium sulphite solution, 8% sodium bicarbonate solution and dried (MgSO$_4$). Evaporation of the solvent gave crude title compound as a colourless oil which was purified by chromatography on silica with ethyl acetate/light petroleum (1:9) as eluent to afford title compound as a pale yellow oil (0.14 g).

EXAMPLE 6

8-anti-(3-t-butyldimethylsilyloxy-1-octenyl)-6-endo-t-butyldimethyl-silyloxy-2-oxabicyclo[3,2,1]octan-3-ol A 20% solution of diisobutyl aluminium hydride (1.0 ml) was added at −70°, under nitrogen, to a solution of 8-anti(3-t-butyl-dimethylsilyloxy-1-octenyl)-6-endo-t-butyldimethylsilyloxy-2-oxabicyclo [3,2,1]octan-3-one (0.496 g) in dry petroleum ether (b.p. 60°–80°) (30 ml) and stirred at −70° for 1½ hr. Water was added followed by 2 N sulphuric acid sufficient to dissolve the precipitate. The organic layer was removed and the aqueous layer extracted once with petroleum ether (b.p. <40°) (20 ml). The combined organic extracts were washed with 2 N sulphuric acid (2×10 ml), once with brine and dried (MgSO$_4$). Evaporation of the solvent gave title compound as a colourless oil (0.55 g).

Rf 0.31 (silica-ethyl acetate/light petroleum (b.p. 60°–80°) (1:9)-dinitrophenyl hydrazine reagent); $\nu_{max}$ (film) 1720, 3400 cm$^{-1}$.

EXAMPLE 7

9α,15α and 15β
Bis-dimethyltertiarybutylsilyloxy-11α-hydroxy-5-cis 13-trans, prostadienoic acid (disilyl protected PGF 2α)

A solution of n-butyllithium in hexane (2.4 M, 1 ml) was added carefully to dry dimethylsulphoxide (3 ml) and the mixture was stirred for a few minutes at room temperature. A solution of (4-carboxybutyl)-triphenyl-phosphonium bromide (0.44 g), in dry dimethylsulphoxide (2–3 ml) was then added whereupon a bright dark orange solution formed which was stirred at room temperature for 15 minutes. A solution of 8-anti-(3-t-butyldimethylsilyloxy-1-octenyl)-6-endo-t-butyldimethyl-silyloxy-2-oxabicyclo [3,2,1]-octan-3-ol (0.55 g) in dimethylsulphoxide (2 ml) and dry tetrahydrofuran (2 ml) was then added to the solution which became pale yellow in a few minutes at room temperature.

The mixture was then stirred (1¾ hr) at room temperature and quenched with water, acidified with sulphuric acid and extracted twice with ether. The bulked ether extracts were washed with water, saturated brine and were dried (MgSO$_4$). Evaporation of the solvent gave a light brown oil which was purified by preparative thin layer chromatography on silica (ethyl acetate/light petroleum (1:4), 3 elutions, the compounds were removed by soxhlet extraction with ether). Complete separation of the two title compounds was achieved. Less polar 9α, 15β isomer obtained as a pale yellow oil 65 mg (A) More polar 9α,15α isomer obtained as a pale yellow oil 127 mg (B) TLC shows complete separation of compound Rf$_A$=0.40, Rf$_B$=0.35.

Analysis of A Found C, 66.32; H, 11.40; $C_{32}H_{61}Si_2O_5$ requires C, 66.04; 10.56%.

Analysis of B Found C, 66.27; H, 11.28; $C_{32}H_{61}Si_2O_5$ requires C, 66.04; H, 10.56%.

EXAMPLE 8

9α,11α,15α-Trihydroxy-5-cis, 13-trans, prostadienoic acid (PGF$_{2α}$)

The disilyl protected PGF$_{2α}$ isomer B prepared as in Example 7 (45 mg) was dissolved in dry tetrahydrofuran (2 ml) and 2N hydrochloric acid (0.5 ml) and the reaction was left at room temperature for 6 days. Diethyl ether (15 ml) was added and the organic phase extracted with water (2×5 ml). The ether solution was dried and transferred to a TLC plate [(20×20 mm). Kieselgel 60F- 254 DC] which was eluted three times (methanol/ethyl acetate (1:24)). The silica was soxhlet extracted with ether and the solvent removed to give title compound as a pale yellow oil (20 mg); Rf 0.28, trace 0.38 (silica-dioxan/benzene/acetic acid (20:20:1)—molybdatophosphoric acid) identical Rf with an authentic sample of PGF$_{2α}$.

EXAMPLE 9

7-anti-Butyl-5-endo-(t-butyldimethylsilyloxy)-bicyclo [2,2,1]heptan-2-one (a) A solution of n-butylmagnesium chloride (1.10 ml of 0.91 M ether solution) in dry ether (2 ml) and dry tetrahydrofuran (3 ml) was cooled to −30° under nitrogen and treated with freshly prepared cuprous chloride (100 mg). The brown suspension was stirred at −30° for 10 minutes and then treated with a solution of 3-endo-(t-butyldimethylsilyloxy)-tricyclo[3,2,0,0$^{2,7}$]heptan-6-one (215 mg) in dry light petroleum (1 ml). After 30 minutes stirring at −30°, the reaction mixture was quenched with saturated aqueous ammonium chloride (10 ml) and extracted with ether (3×20 ml). The combined ether extracts were dried (MgSO$_4$) and evaporated to give an oil (259 mg). Preparative thin layer chromatography on silica [EtOAc/light petroleum (1:24)] gave title compound (91 mg) as a colourless crystalline solid, m.p. 43°-53°. Rf 0.54 (silica-EtOAc/light petroleum (3:7) - dinitrophenylhydrazine reagent) $v_{max}$ (CHBr$_3$) 1738 cm$^{-1}$.

(b) A solution of n-butylmagnesium chloride (1.0 ml of 0.91 M ether solution) was cooled to −25° under nitrogen and treated with a solution of cupric acetate monohydrate (8 mg) in dry tetrahydrofuran (0.5 ml) with stirring. The colourless suspension was cooled with stirring to −35° and treated slowly dropwise with a solution of 3-endo-(t-butyldimethylsilyloxy)-tricyclo [3,2,0,0$^{2,7}$]heptan-6-one (185 mg) in dry tetrahydrofuran (1.0 ml). The yellow brown solution was stirred at −35° for 30 minutes, quenched with saturated aqueous ammonium chloride (5 ml) and extracted with ether (3×10 ml). The combined ether extracts were dried (MgSO$_4$) and evaporated to give an oil which was purified by preparative thin layer chromatography on silica (EtOAc/light petroleum (1:19), 2 elutions) to give title compound (80 mg) as a colourless crystalline solid.

EXAMPLE 10

5-endo-(t-Butyldimethylsilyloxy)-7-anti-[3-[(tetrahydro-2H-pyran-2-yl)oxy]-1-propynyl]-bicyclo[2,2,1]heptan-2-one A solution of tetrahydro-2-(3-propynyloxy)-2H-pyran (266 mg) in dry tetrahydrofuran (1.0 ml) was added slowly dropwise to stirred n-butyllithium (1.0 ml of 1.9 M solution in hexane) at −78° under nitrogen. The straw-coloured solution was stirred at −78° for 10 minutes, −20° for 20 minutes, and then treated at −78° with a solution of 3-endo-(t-butyl-dimethylsilyloxy)-tricyclo [3,2,0,0$^{2,7}$]heptan-6-one (452 mg) in dry tetrahydrofuran (1.0 ml) with stirring. The resulting mixture was allowed to warm slowly to −5° over a period of 17 hours with stirring under nitrogen, quenched with saturated aqueous ammonium chloride (10 ml) and extracted with ether (4×20 ml). The combined ether extracts were dried (MgSO$_4$) and evaporated to give a pale straw-coloured oil.

Preparative thin layer chromatography on silica (EtOAc/light petroleum (3:7), 1 elution) gave a pale yellow oil (390 mg) [Rf 0.36 (silica EtOAc/light petroleum (b.p. 60°-80°) (3:7)-dinitrophenylhydrazine reagent)]. Further purification of 250 mg of this oil by preparative thin layer chromatography on silica (ether/benzene (1:9), 3 elutions) gave title compound (23 mg) as a colourless oil.

R$_f$ 0.55 (silica - 3 elutions with ether/benzene (1:9) - deep yellow with dinitrophenylhydrazine reagent) $v_{max}$ (film) 1748 cm$^{-1}$.

EXAMPLE 11

3-endo-Triphenylsilyloxy-tricyclo[3,2,0,0$^{2,7}$]heptan-6-one

To a stirred solution of potassium butoxide (1.0 g) in dry tetrahydrofuran (22 ml) at −70° was added 2-exo-bromo-3-endo-triphenylsilyloxy-bicyclo[3,2,0]heptan-6-one (3.75 g) in dry tetrahydrofuran (8 ml) dropwise. After 0.75 hour a further portion of potassium butoxide (0.95 g) and tetrahydrofuran (12 ml) was added. The mixture was allowed to warm to 0°, diluted with ether (100 ml) and stirred with Hyflo and charcoal for 2 minutes. The solution was filtered through Hyflo, washing the pad with ether (50 ml). The mother liquors were evaporated to dryness at room temperature to give title compound as a white solid (3.35 g). R$_f$0.35 (silica - ethyl acetate/petroleum ether b.p. 60°-80° (1:1)-dinitrophenylhydrazine and UV).

EXAMPLE 12

5-endo-Triphenylsilyloxy-7-anti-[3-t-butyldimethyl-silyloxy-1-octenyl]-bicyclo[2,2,1]heptan-2-one To a solution of 3-t-butyldimethylsilyloxy-1-iodo-1-octene (3.0 g) in dry ether (5 ml) at −70° was added 1.6

M n-butyllithium (50 ml, 0.008 m) in hexane and the mixture stirred for 0.5 hour. A filtered solution of cuprous pentyne (1.04 g) in hexamethylphosphorus triamide (3.0 ml) and ether (10 ml) was added to this solution and stirred for 15 minutes at −70°. To the resultant solution was added 3-endo-triphenylsilyloxy-tricyclo[3,2,0,0$^{2,7}$]heptan-6-one (3.1 g) in tetrahydrofuran (12 ml). A further portion of tetrahydrofuran (20 ml) was added after 2 hours and the reaction left for 1 hour at −70°. Saturated ammonium chloride (25 ml) was added to the cold solution and allowed to warm to room temperature. The aqueous portion was separated and extracted with ethyl acetate (20 ml). The combined organic extracts were washed with 5N hydrochloric acid (20 ml), water (20 ml) and dried (MgSO$_4$). Removal of solvent gave a yellow oil containing a white solid which was treated with ether, filtered and the ether soluble portion evaporated to dryness to give a yellow oil (4.7 g). The oil was chromatographed on silica (250 g). Ethyl acetate/petroleum spirit b.p. 60°–80° (1:19) eluted unreacted octene side chain and elution with ethyl acetate/petroleum spirit b.p. 60°–80° (1:9) followed by evaporation of solvents afforded pure title compound (0.9 g) as a colourless oil. R$_f$ 0.4 (silica - ethyl acetate/petroleum spirit b.p. 60°–80° (3:17)-dinitrophenylhydrazine-UV)

Analysis Found C, 75.40; H, 8.69; C$_{39}$H$_{52}$Si$_2$O$_3$. Requires C, 75.07; H, 8.40%.

EXAMPLE 13

3-endo-(Benzyloxy)tricyclo[3,2,0,0$^{2,7}$]heptan-6-one

Potassium t-butoxide (20.58 g) was added to dry tetrahydrofuran (220 ml) at −78° under nitrogen and dissolved with stirring. The cloudy solution was treated at −78° with a solution of 2-exo-bromo-3-endo(benzyloxy)-bicyclo[3,2,0]heptan-6-one (48.13 g) in dry tetrahydrofuran (60 ml). After 1 hour at −78° the mixture was warmed to 0°, diluted with dry ether (300 ml) and filtered through a pad of Hyflo under nitrogen. The Hyflo pad was washed with ether (3x). The colourless filtrate was concentrated at 10°/1–5 torr to an oil (ca 40 g), then at 20°/0.5 torr to give title compound as a colourless crystalline solid (31.18 g). Crystallisation from light petroleum (b.p. 40°–60°) gave colourless crystals, m.p. 58.5°–60.5°. R$_f$ 0.22 (silica-EtOAc/light petroleum (b.p. 60°–80°) (1:1)-dinitrophenylhydrazine reagent) $\nu_{max}$ (Nujol) 1728, (CHBr$_3$) 1750, (CCl$_4$) 1765 cm$^{-1}$.

EXAMPLE 14

7-anti[3[(1,1-Dimethylethyl)dimethylsilyloxy]-1-octenyl]-5-endo-phenyl-methoxybicyclo[2,2,1]heptan-2-one Hexamethylphosphorus triamide (7.7 ml; 4×10$^{-2}$ m) was added dropwise at room temperature to a stirred suspension of copper pentyne (2.8 g) in dry ether (10 ml). After 30 min. the solution was filtered and the residue discarded.

A solution of n-butyl lithium (13 ml of 1.6 M hexane solution; 2×10$^{-2}$m) was added dropwise at −70° under a nitrogen atmosphere to a stirred solution of 3[(1,1-dimethylethyl)dimethylsilyloxy]-1-iodo-1-octene (7.6 g) in dry ether (30 ml), and stirring continued for 15 min. The above copper (I) solution was added dropwise at −70° and the mixture stirred for 30 min. A solution of 3-endo-phenylmethoxy-tricyclo[3,2,0,0$^{2,7}$]heptan-6-one (4.4 g) in dry tetrahydrofuran (30 ml) was added dropwise to the stirred solution. The reaction was quenched after 50 min, by the addition of saturated ammonium chloride solution (50 ml). This mixture was allowed to warm to ambient temperature and the organic layer removed and shaken with ice-cold 2N sulphuric acid (30 ml). The precipitated salts were filtered off and the organic layer removed from the filtrate, washed with water (50 ml) and dried (Na$_2$SO$_4$). Evaporation of the solvent afforded a viscous yellow oil (6.1 g) which was chromatographed on silica gel (Kieselgel 70–230 mesh; 120 g) collecting 100 ml fractions.

Elution with ethyl acetate/petroleum ether (b.p. 60°–80°) (1:19) and fractionation, followed by evaporation of solvent gave the title compound in fractions 16–24 as a pale yellow oil (3.5 g). TLC: Single spot R$_f$ 0.62 (silica gel-ethyl acetate/petroleum ether (1:4)-molybdophosphoric acid) $\nu_{max}^{CHBr_3}$: 1740 (>C=O), 970 (trans C=C) cm$^{-1}$ NMR: 2.65 (5H, s, Ph); 4.4. (2H, m, —HC=CH—); 5.5. (2H, s, —CH$_2$Ph)$\tau$ Assay Found: C, 73.7; H, 10.1; C$_{28}$H$_{44}$SiO$_3$. Requires: C, 73.63; H, 9.71%.

The following compounds were similarly prepared:

(a) 7-anti[3[(1,1-Dimethylethyl)dimethylsilyloxy]-1-octenyl]-5-endo-(tetrahydro-2H-pyran-2-yloxy)bicyclo[2,2,1]heptan-2-one, as a colourless oil.

TLC: Single spot R$_f$ 0.42 (silica gel-ethyl acetate/petroleum ether (1:4)-molybdophosphoric acid) $\nu_{max}^{film}$: 1750 (>C=O) cm$^{-1}$ NMR: 4.4 (2H, m, CH=CH)$\tau$ (b) 7-anti[3[(1,1-Dimethylethyl)dimethysilyloxy]-1-decenyl]-5-endo phenylmethoxybicyclo[2,2,1]heptan-2-one as a colourless oil, isolated by chromatography.

TLC: Major component R$_f$ 0.65 (Silica gel - ethyl acetate/petroleum ether (1:4) - molybdophosphoric acid).

$\nu_{max}^{CHBr_3}$: 1740 (C=O), 970 (trans C=C) cm$^{-1}$

NMR (CDCl$_3$): 2.65 (5H, s, Ph); 4.2–4.7 (2H, m, CH=CH); $\tau$ 5.52 (2H, s, PhCH$_2$)

Assay Found: C, 74.08; H, 10.18; C$_{30}$H$_{48}$SiO$_3$. Requires: C, 74.32; H, 9.98%.

(c) 7-anti[3-methyl-3-(trimethylsilyloxy)-1-octenyl]-5-endo-phenylmethoxy-bicyclo[2,2,1]heptan-2-one as a colourless oil, isolated by chromatography.

TLC: Single spot R$_f$ 0.66 (silica gel-ethyl acetate/light petroleum (60°–80°) (1:4) - molybdophosphoric acid).

$\nu_{max}^{film}$: 1745 (C=O)

$\tau$(CDCl$_3$): 2.67 (5H, s, Ph); 4.33–4.6 (2H, m, CH=CH); 5.53 (2H, s, PhCH$_2$); 8.73 (3H, s, —C(OSiMe$_3$)CH$_3$); 9.91 (9H, s, —Si(CH$_3$)$_3$)

Assay Found: C, 72.54; H, 9.47; C$_{26}$H$_{40}$O$_3$Si Requires: C, 72.84; H, 9.41%

(d) 7-anti[3[(1,1-Dimethylethyl)dimethylsilyloxy]-1-undecenyl]-5-endophenyl-methoxybicyclo[2,2,1]heptan-2-one as a colourless oil, isolated by chromatography.

TLC: Single spot R$_f$ 0.50 (silica gel - ethyl acetate/petroleum ether (1:4) - molybdophosphoric acid).

$\nu_{max}^{CHBr_3}$: 1740 (C=O), 970 (trans C=C) cm$^{-1}$ $\tau$(CDCl$_3$): 2.63 (5H, s, Ph); 4.2–4.7 (2H, m, HC=CH); 5.5 (2H, s, —CH$_2$Ph)

Assay Found: C, 74.19; H, 10.47; C$_{31}$H$_{50}$O$_3$Si Requires: C, 74.64; H, 10,10%

EXAMPLE 15

8-anti-Butyl-6-endo-methoxy-2-oxa-bicyclo[3,2,1]octan-3-ol

A solution of 8-anti-butyl-6-endo-methoxy-2-oxabicyclo[3,2,1]octan-3-one (1.69 g) (Example 4) in dry redistilled tetrahydrofuran (14 ml) was cooled to −65° under nitrogen and a 20% hexane solution of di-isobutyl aluminium hydride (8.5 ml) was added dropwise. The mixture was stirred at −65° for three hours. After quenching by the addition of water (50 ml) the solution was allowed to warm to room temperature and acidified with 2 N sulphuric acid (50 ml). The organic phase was removed and the aqueous layer was extracted with ether (40 ml). The combined organic fractions were washed with 2 N sulphuric acid (2×50 ml), saturated brine (100 ml) and dried. Evaporation of solvent afforded the title compound as a pale yellow oil (1.8 g).

EXAMPLE 16

7-(2-n-Butyl-3-hydroxy-5-methoxycyclopentyl)-5-heptenoic acid (1α,2β-3α,5α)

The process of Example 7 was followed using 15 ml of 1.9 M n-butyllithium in hexane added to 35 ml of dry dimethylsulphoxide. 6.23 g of (4-carboxybutyl) triphenylphosphonium bromide were added and 1.5 g of 8-anti-n-butyl-6-endo-methoxy-2-oxabicyclo[3,2,1]octan-3-ol were employed.

1.4 g of title compound were obtained.

Found C 68.22 H 10.03%. $C_{17}H_{30}O_4$ Requires C 68.42 H 10.13%.

We claim:

1. A compound of the formula

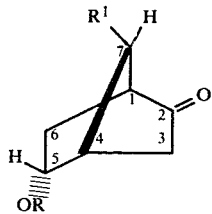

wherein R is acyl, tri(hydrocarbyl)silyl or tetrahydropyranyl and $R^1$ is an optionally substituted $C_{1-12}$ aliphatic group.

2. A process for the preparation of a compound as claimed in claim 1, comprising reacting a compound of the formula

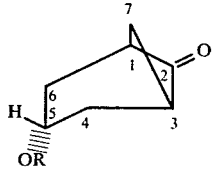

wherein R is acyl, tri(hydrocarbyl)silyl or tetrahydropyranyl with an organometallic reagent serving to introduce the group $R^1$ as defined in claim 1 at the 7-position of the bicyclo[2,2,1]heptan-2-one system.

3. A process as claimed in claim 2 wherein the organometallic reagent is a copper-containing reagent of the type Li[$R^2$ Cu $R^{1a}$] wherein $R^{1a}$ is as defined for $R^1$ other than an ethynyl, or 2-subsituted ethynyl group; and $R^2$ is the same as $R^{1a}$ or is an ethynyl or 2-substituted ethynyl group;

a lithium-aluminium complex of the type Li Al $(R^3)_3R^{1b}$ wherein the groups $R^3$ represent alkyl groups which may be the same or different and $R^{1b}$ represents an alk-1-enyl group;

a Grignard reagent $R^{1c}$ MgX wherein $R^{1c}$ is as defined for $R^1$ and X represents a halogen atom;

an organocopper reagent Cu$(R^{1a})_2$ wherein $R^{1a}$ is as defined above in the presence of a magnesium or lithium halide;

a copper-containing reagent of the formula Li[$R^2$ Cu $R^{1a}(R^4)_2$] wherein $R^2$ and $R^{1a}$ are as defined above and $R^4$ is phosphorus-containing organic or a lithium acetylide of the type Li$R^{1d}$ wherein $R^{1d}$ is an ethynyl or 2-substituted ethynyl group.

4. A process as claimed in claim 3 wherein the Grignard reagent is employed in the presence of a copper-containing catalyst.

5. A process as claimed in claim 2 wherein $R^1$ represents a straight or branched chain alkyl, alkenyl or alkynyl group of from 1–12 carbon atoms, which may be unsubstituted or substituted.

6. A process as claimed in claim 2 in which R is an alkanoyl group containing not more than 7 carbon atoms; an aralkanoyl or aroyl group containing not more than 20 carbon atoms; a tri(hydrocarbyl)silyl group containing three hydrocarbyl substituents which may be the same or different, selected from the group consisting of $C_{1-6}$ alkyl, $C_{2-6}$ alkenyl, $C_{3-7}$ cycloalkyl, $C_{7-20}$ aralkyl and $C_{6-20}$ aryl groups.

7. A compound of the formula (I)

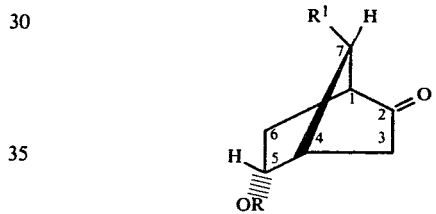

wherein R represents an acyl, tri(hydrocarbyl)silyl, alkyl, aralkyl, cycloalkyl or tetrahydropyranyl group, and $R^1$ represents an optionally substituted $C_{1-12}$ aliphatic group.

8. A compound as claimed in claim 7 wherein R represents an alkanoyl group containing not more than 7 carbon atoms; an aralkanoyl or aroyl group containing not more than 20 carbon atoms; a tri(hydrocarbyl)silyl group containing three hydrocarbyl substituents, which may be the same or different, selected from $C_{1-6}$ alkyl, $C_{2-6}$ alkenyl, $C_{3-7}$ cycloalkyl, $C_{7-20}$ aralkyl and $C_{6-20}$ aryl groups; an alkyl group containing up to 6 carbon atoms; a $C_{3-7}$ cycloalkyl group; or an aralkyl group containing up to 20 carbon atoms and $R^1$ represents a straight or branched chain alkyl, alkenyl or alkynyl group of from 1–12 carbon atoms, which may be unsubstituted or substituted by a phenyl, substituted phenyl, $C_{3-7}$ cycloalkyl, $C_{5-7}$ cycloalkenyl or hydroxyl or protected or substituted hydroxyl group or halogen atom.

9. A compound as claimed in claim 8 wherein the group R represents an acetyl, trimethylsilyl, t-butyldimethylsilyl, triphenylsilyl, methyl, benzyl, tetrahydropyranyl 2-methoxy-ethoxymethyl, 1-methoxyethyl or 1-ethoxy-ethyl group, and $R^1$ represents a $C_{3-12}$ alkyl, alkenyl or alkynyl group optionally carrying a keto or protected keto group and optionally substituted by a hydroxyl or protected or substituted hydroxyl group.

10. A compound as claimed in claim 7, wherein R' represents a group of formula

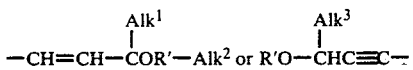

group wherein R' is acyl, tri(hydrocarbyl)silyl, alkyl, aralkyl, cycloalkyl, tetrahydropyranyl or hydrogen, Alk¹ represents hydrogen or an alkyl group having up to 2 carbon atoms and Alk² represents an alkyl group having up to 9 carbon atoms and Alk³ represents hydrogen or an alkyl group having up to 9 carbon atoms.

11. A compound of the formula

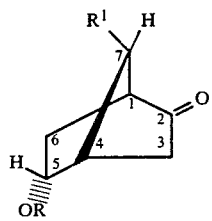

wherein R is tri(hydrocarbyl)silyl and R¹ is an unsubstituted straight or branched chain alkyl, alkenyl or alkynyl group of from 1-12 carbon atoms or such a group substituted by a hydroxy or tri(hydrocarbyl)silyloxy group.

12. A process for the preparation of a compound as claimed in claim 11, comprising reacting a compound of formula

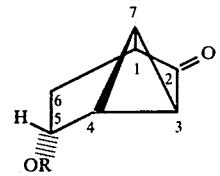

wherein R is tri(hydrocarbyl)silyl with an organometallic reagent serving to introduce the group R¹ as defined in claim 11 at the 7-position of the bicyclo[2,2,1]-heptan-2-one system.

13. A compound as claimed in claim 1, wherein R is tri(hydrocarbyl)silyl.

14. The process as claimed in claim 2, wherein R is tri(hydrocarbyl)silyl.

* * * * *

UNITED STATES PATENT AND TRADEMARK OFFICE
CERTIFICATE OF CORRECTION

PATENT NO. : 4,181,674
DATED : January 1, 1980
INVENTOR(S) : Roger F. Newton et al.

It is certified that error appears in the above-identified patent and that said Letters Patent are hereby corrected as shown below:

IN THE CLAIMS:

Claim 2, column 19, after line 3, correct the structural formula to read:

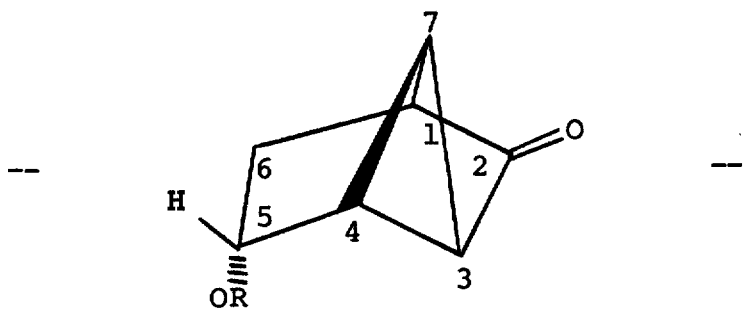

Signed and Sealed this

Seventeenth Day of June 1980

[SEAL]

Attest:

SIDNEY A. DIAMOND

Attesting Officer     Commissioner of Patents and Trademarks